(12) United States Patent
Arkoff et al.

(10) Patent No.: US 11,693,990 B1
(45) Date of Patent: Jul. 4, 2023

(54) MEDICAL DATA GOVERNANCE

(71) Applicants: Harold Arkoff, Sudbury, MA (US);
Vedran Jukic, Trieste, MA (US)

(72) Inventors: Harold Arkoff, Sudbury, MA (US);
Vedran Jukic, Trieste, MA (US)

(73) Assignee: OneSource Solutions International, Inc

( * ) Notice: Subject to any disclaimer, the term of this patent is extended or adjusted under 35 U.S.C. 154(b) by 0 days.

(21) Appl. No.: 17/990,085

(22) Filed: Nov. 18, 2022

Related U.S. Application Data

(63) Continuation of application No. 16/812,282, filed on Mar. 7, 2020, now Pat. No. 11,532,393.

(51) Int. Cl.
*G16H 40/20* (2018.01)
*G06F 21/62* (2013.01)
*G06F 21/60* (2013.01)

(52) U.S. Cl.
CPC ........ *G06F 21/6254* (2013.01); *G06F 21/602* (2013.01); *G16H 40/20* (2018.01)

(58) Field of Classification Search
CPC .... G06F 21/6254; G06F 21/602; G16H 40/20

USPC ........................................................ 705/2–3
See application file for complete search history.

(56) References Cited

U.S. PATENT DOCUMENTS

| | | | |
|---|---|---|---|
| 9,886,558 B2* | 2/2018 | Ober | G16H 20/00 |
| 2007/0021979 A1* | 1/2007 | Cosentino | A61B 5/0031 |
| | | | 600/300 |
| 2015/0332283 A1* | 11/2015 | Witchey | G16H 10/60 |
| | | | 705/3 |
| 2018/0060496 A1* | 3/2018 | Bulleit | H04L 9/0643 |
| 2018/0122506 A1* | 5/2018 | Grantcharov | G16H 50/50 |

\* cited by examiner

*Primary Examiner* — Michael Tomaszewski
(74) *Attorney, Agent, or Firm* — IP Consulting Group; Michael Razavi; Alfred F. Hoyte, Jr.

(57) ABSTRACT

A medical data governance system records, secures, and provides appropriate access to all patient data. By concentrating all available relevant medical data into a single source, and providing a subset of data to each receiving subsystem with the correct source and time reference, the medical data governance system becomes the true source of data and guarantees the data consistency through the use of block chain signatures.

12 Claims, 9 Drawing Sheets

MEDICAL DATA GOVERNANCE

FIELD OF THE INVENTION

This application relates to healthcare data management hardware and software, and more particularly to reliable medical device data interoperability and storage in a normalized, standardized format useful for healthcare providers and medical research.

BACKGROUND

Modern hospitals are complex, technologically sophisticated organizations having sometimes thousands of employees, doctors, nurses, medical technicians, and administrators, with critical life or death decisions being made regularly, and sometimes having to be made abruptly and quickly. Up-to-date, perspicuous, and complete data about the patient can make a difference. And even when critical decisions are not at stake, increases in the cost of health care have made it imperative to use patient data, facility personnel and resources as efficiently as possible.

Medical Data Governance is an approach to managing data that allows hospitals and health organizations to balance two needs: the need to collect and secure all available information while also maximizing the usefulness of that information for patient care, medical research and other valid purposes. Patient data collected during operations, other medical procedures and patient recovery is updated continually and often needs to be displayed immediately and in an efficient and speedily apprehended manner to attending medical personnel as well as being permanently retained in a standard format useful to facility management and medical researchers among others who may be in remote locations and/or need to compare data from myriad healthcare facilities.

Nowadays governments try to limit legal collection of personal data through various privacy protection acts. By doing so, they limit the collection of data for future research or for validation at the time of data collection. Medical Data Governance (MDG) absolves the important role of governing the process of acquisition, patient identification, provider identification, data validation, time synchronization, localization of different, non-homogeneous clinical, medical, medical relevant, and patient relevant data from isolated, standalone medical devices or networked devices. MDG fulfills the need for a true and complete source of data for other consumers of medically relevant data, such as Electronical Medical Records, Health Medical Records, Artificial Intelligence systems, Machine Learning systems, research, trials, Decision Support Systems, data recording and so on. The process of collection, normalization, association of data, along with source localization, type, quality and anonymous metadata, allow customizable subsets of data to be provided to different accredited users, systems and endpoints. Some of the use cases of MDG are innovative, and some represent more efficient, cost effective methods compared to already existing procedures or methods.

Artificial Intelligence and Machine Learning systems require a medical data governance middleware to assure proper, normalized and verified data inputs. Legacy health information systems and electronic medical records were designed to receive only a portion of the exponentially increasing data medical devices can create and can be collected. Further, outdated HIS/EMR (Healthcare Information Systems/Electronic Medical Record) and inadequate patient identification and association can cause a serious bottleneck for data-hungry personalized medicine, real time applications, and in practice, most medical device data are not recorded at all. And yet as shown in recent studies it can be easy to identify individuals even from anonymized data.

SUMMARY

In accordance with the present disclosure, embodiments of a system, method, and apparatus are described which eliminate or ameliorate the problems and disadvantages associated with previous systems, methods, and apparatuses.

Due to the exponential data availability from growing health-related devices, the risk of data not being collected, or worst, being wrongly associated, grows exponentially. In particular embodiments, the MDG opposes this trend by using the same data to augment the data affinity and isolate and indicate possible association or data integrity errors.

When errors are detected from automated systems or from a later check or evidence, errors are propagated through related data, and when the data, a wrong association or time reference is corrected and signed with block-chain, the whole time segment of the data must be resent to the subsystem. Particular embodiments include the Medical Data Governance System (MDGS) as the true and complete source of data which should be used as the front end for subsystems.

By concentrating all available medical relevant data into a single source, and providing a subset of data to each receiving subsystem with the correct source and time reference, the Medical Data Governance System becomes the true source of data and guarantees the data consistency through the use of block chain signatures.

The instant invention provides a simple, stress-free, inexpensive connection and data-combining scheme requiring no special effort or consideration on the part of the medical personal attempting to care for patients in a wide range of hospital settings.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
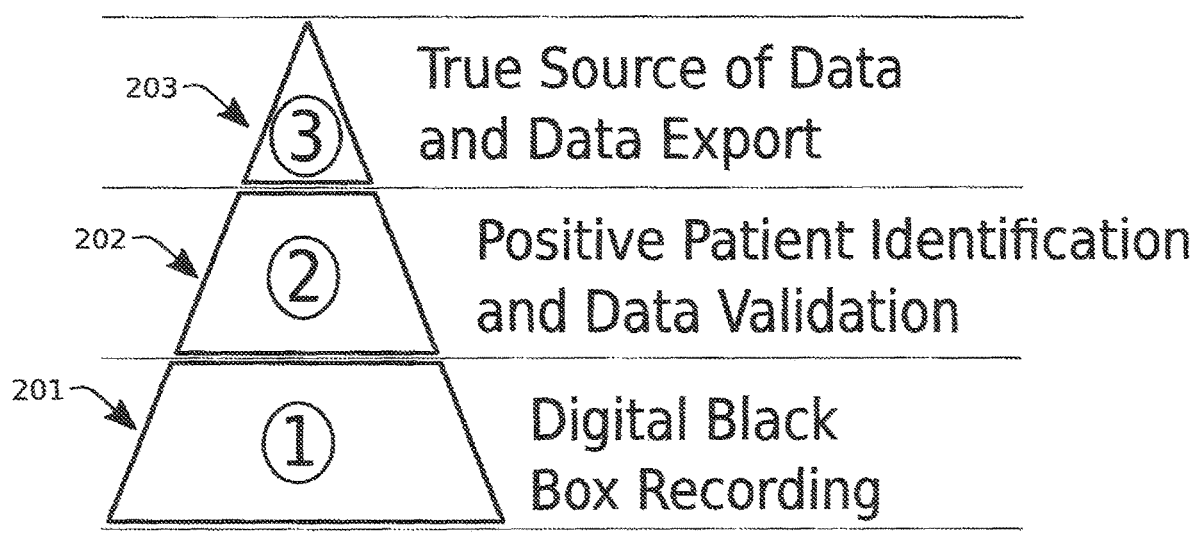
FIG. 1 is a block diagram overview of a Medical Data Governance system (MDGS) according to an embodiment of the invention.

FIG. 1 is a block diagram overview of the three functional layers of a Medical Data Governance System (MDGS) in an embodiment. The base layer 201 is digital black box recording of patient data. The middle layer 202 is positive patient identification and data validation. The top layer 203 is true source data and data export for research and other purposes.

Binding location (geo-localization, indoor localization), time, provider, and patient is associated with data obtained from isolated or networked medical and medical relevant devices. The MDG system collects data from medical devices, identifies them, normalizes and time synchronizes all the data outputs while storing them safely, with tamper detection methods (such as blockchain) local to the source of data. Partial and/or metadata about the collected data are used to identify the related patient, patient location, patient provider, source of data and location from whom the data had been collected when available. In the process described as MDG, the normalized data along with time, time span (or duration), location, and patient ID are securely stored and saved for data export into third party systems (data consumers) or stored for later export. The process of binding location, time, provider, and patient identification to the data can occur pre or post data collection, generating a new dataset at each intervention or association, creating incremental dataset groups. For example, complete patient association can be done hours or days after the data had been collected, as well preset before the data is collected from the medical device.

Patient Treatment Time Optimization and Device Asset Management

MDG provides a true source of data that can highlight the schedule time variations of exams and other medical treatments and provides tools for rescheduling feedbacks, contacting and receiving feedbacks from patients/physician/healthcare professionals thus introducing general system flexibility through the use of lean process and six sigma methods.

MDG leverages modern communication methods (phone apps, emails, web services, etc.) and easily links patient and physicians or other healthcare professionals to the scheduled use of medical devices.

After unexpected events that may cause a miss in scheduled operations, the MDG may create a backup schedule to preemptively fill the gaps and may facilitate healthcare and schedule professionals to optimize machine time usage. This could create a new marketplace for priority services for those patients that opt for it.

Patient/User Data Monetization by Patient/User, Institution or Combination of

MDG enables patients/users and or institutions to monetize their vital, medically relevant, patient data collected during the stay inside the healthcare institution, as well through the extended data collected over period of time in a multiple stays or spot measurements in healthcare institutions. Patients could establish a relationship with a third party (such as drug manufacturer, independent drug trial projects, undisclosed trials to the institution) and provide to the third party normalized data collected, organized and provided by the MDG used by the healthcare institution, and provided to the patient in different standardized format, even in near real time. The institution might not be aware of the final user of the patient data. MDG can create additional revenue to the institution by charging such a service per patient and per data processed. MDG can track and trace data usage per patient and assets. MDG through the export of all specific, validated clinical data, medical relevant data, could create a new data-based economy.

Patient Notification and Pre or Post Consent of Data Use for Second Opinions, Medical Treatments, Specific Research, Validation, Education or Application.

MDG manages patient consent and approval, or notification for use of the patient data for second opinion, medical treatments, specific research, validation projects, and educational purposes. Specific patient or user data is previously screened based on always updated, public, generic, anonymous metadata (for example: sex, age, days in hospital, normalized data content and length: heart rate, respiration rate, drugs, etc.)

MDG can handle patient consent using modern communication methods (phone apps, emails, web services, etc.) and provide patient consent for his data to be used in a specific research or validation project, with or without compensation. MDG can provide patient consent and access to the data to specific users, like doctors, physicians, and other specific medical professionals. MDG can provide specific code associated to the data, that, based on necessity, can provide, if granted by the user or proxy consent, protected personal identification, family relations or other protected personal data.

Research Dataset Optimization

MDR allows for third party statistical analysis (research) on the whole population dataset, without exporting or providing data to the third party, but rather comparing the result to the legally available consent subset group. A statistically relevant result might indicate a minimal group of statistically significant subset of data to search consent and optimize the time for valid and repeatable dataset.

Data Normalization

Data normalization appears to be a key element for application of Artificial Intelligence in Healthcare. MDG, through the acquisition of higher frequency (sub-minute/sub-seconds), high fidelity data, patient identification, provider identification, data validation, time synchronization, localization of different, non-homogeneous clinical, medical relevant, patient relevant data from isolated, standalone medical devices or networked devices, can provide a superior, in terms of quality and quantity, subset of normalized data.

Metadata

MDG collects and stores all available data from any potential source of data, localizes and time synchronizes all data points. Metadata such as, healthcare provider, environment temperature, hours of operation of medical device, time from last service, related errors can provide almost endless source of data for future use or research.

An Overall Solution to the Lack of Standards and Interoperability

MDG, as a sole purpose of true source of data, and without any specific end user purpose serves as an interoperability and standardization tool, enabling the health industry to leverage stored data through new and old standards based on the need.

Root-Cause Analysis and Quality Improvement Classification

As a most complete data gathering and presentation tool, any adverse case or event can be studied up to the maximum details recorded by the MDG. MDG tools help retrieving patient identification, provider identification, data validation, time synchronization, localization of different, non-homogeneous clinical, medical, medical relevant, and patient relevant data after adverse events, providing tools for analyzing risks, therefore introducing quality, process, outcome improvements. This classifies MDG as a quality improvement tool, therefore protected from a legal perspective to be used as a proof of malpractice or errors.

Non-medical user notification and pre or post consent of data use for specific research, validation, education, marketing or application. The ability of handling critical data can be extended to several personal user data in different fields outside of medical.

MDG solves the problem of giving consent and approval, or notification for use of the user data for specific research, validation project, educational purposes, marketing, or application. Specific user data is previously screened based on always updated, public, generic, anonymous metadata (for example: sex, age, days in hospital, normalized data content and length). MDG can handle user consent using modern communication methods (phone apps, emails, web services, etc.) and provide user consent for his data to be used in a specific research or validation project, with or without compensation.

Figure 2:
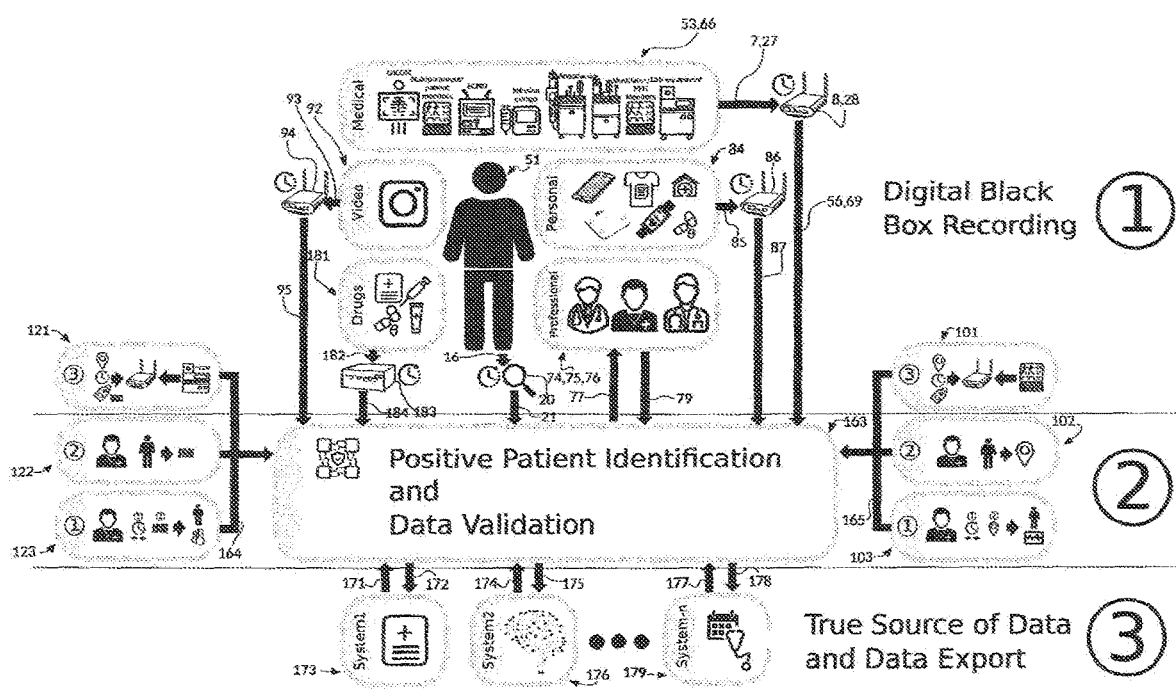
FIG. 2 is an illustration providing high-level detail about each layer of the MDGS pyramid of FIG. 1.

FIG. 2 is an illustration of a simplified 3-layer MDGS in an embodiment. Artificial Intelligence and Machine Learning systems require a medical data governance middleware to assure proper, normalized and verified data inputs. Legacy health information systems and electronical medical records were designed to receive only a portion of the exponentially increasing data medical devices can create and can be collected. Also, outdated HIS/EMR (Healthcare Information Systems/Electronic Medical Record) and inadequate patient identification and association can cause a serious bottleneck for data-hungry personalized medicine, real time applications, and in practice, most medical device data are not recorded at all.

Layer (1): Black Box Recording

Hospital medical devices, continuous monitoring systems and laboratory devices 53, 66, through the use of proper physical and software drivers 7, 27 are collected by Medical Device Data System (MDDS) devices 8, 28 and location/time synchronized, optionally signed with block chain service, and made available to the second layer of the MDG—Positive Patient Identification and Data Validation.

Similar to laboratory devices, video 92 can be transferred 93, recorded 94, location/time synchronized, and then transferred when convenient 95 to a central repository and patient locked by the second layer. Wearables and home or community care data and sensors 84, generally available through BLE (Blue Tooth Low Energy, BT4.1) wireless protocol 85, can be registered and time synchronized by portable MDDS device or phone application 86, and available or optionally transferred 87 when possible to a central repository.

Professional notes, comments, orders and communications, generally known as journaling, 74, 76 can be tracked, reported and stored 77, 79 via third party systems and solutions.

Drug Distribution, Administration and all other third party software and systems 181, 182, 183 can be tracked, tagged, stored, time synchronized and made available 184 to the second layer.

Each MDDS has a location 101 and metadata configuration panel available for setup 121 so the medical device data can be location or patient tagged for patient data association and data validation.

Layer (2): Positive Patient Identification (PPI) and Data Validation (DV)

As described below in more detail in the description of FIG. 5, PPI and DV depends on the previous location and metadata setup of MDDS 121, 101 (FIG. 2) and proper data entry of metadata 122 or location 102, and active healthcare professional confirmation of patient location time presence 103 or the proper patient identification process 123. Upon PPI and DV, different segments of Digital Black Box recordings are patient and time segment tagged 163 and available to the third layer, True Source of Data and Data Export.

Layer (3): True Source of Data and Data Export

By concentrating all available medical relevant data into a single source, and providing a subset of data to each receiving sub-system 173, 176, 179 with the correct source and time reference, the Medical Data Governance System becomes the true source of data and guarantees the data consistency through the use of block chain signatures.

Due to the exponential data availability from growing health-related devices, the risk of data not being collected, or worst, being wrongly associated, grows exponentially. The MDGS opposes this trend by using the same data to augment the data affinity and isolate and indicate possible association or data integrity errors.

The MDGS, as the true and complete source of Data, should be used as the front end for sub-systems. When errors are detected from automated systems or from a later check or evidence, errors are propagated through related data, and when the data, a wrong association or time reference is corrected and signed with block-chain, the whole time segment of the data must be resent to the sub-system rather than those subsystems being corrected independently.

Each medical subsystem 173, 176, 179 is designed to receive specific data with a specific frequency, quantity, and quality. Sometimes the specific data, frequency, quantity, and quality do not overlap between subsystems. From the true source of data, the specific export drivers 171, 172, 174, 175, 177, 178 collect, filter, consistency check, transform and deliver appropriate data to each subsystem.

Figure 3:
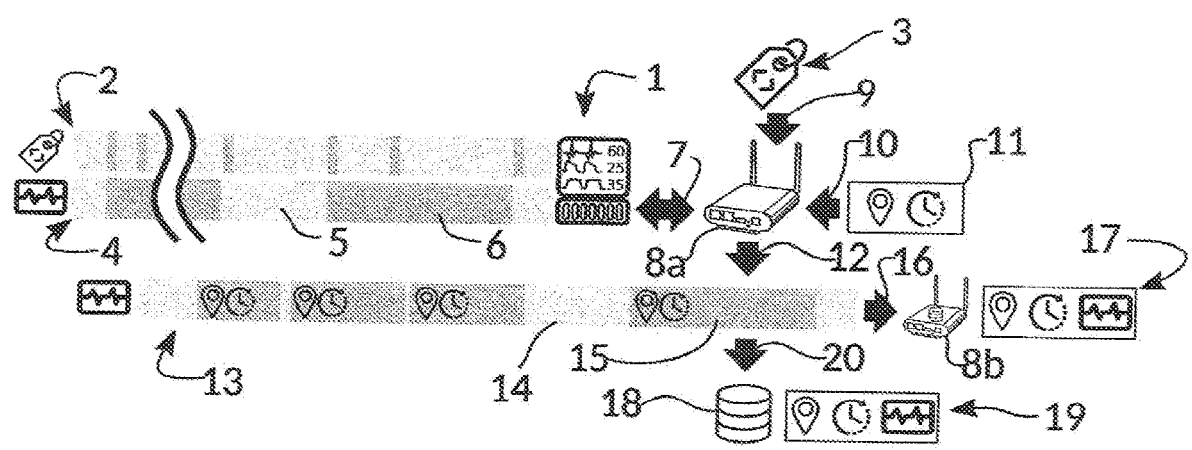
FIG. 3 is an illustration of the details of continuous patient monitoring measurement, part of the first layer of MDGS, Digital Black Box Recording, in an embodiment.

FIG. 3 is a block diagram illustrating details of one component of Layer (1) Digital Black Box Recording, in particular, the medical devices that measure continuous patient data, such as data from multiparametric patient monitoring, anesthesia machines, EEG and similar devices belonging to the "continuous" group of potentially retrievable medical data 4, where the session beginning, duration and therefore, its end can be associated using continuous, complete data flow without data interruption 6. Previous idle, non-patient data that is irrelevant and does not provide any information, except the fact that at that time patient data was not being collected is noted 5. Metadata such as device not ready, cable disconnected, device powered off is recorded 2, including but not limited to room temperature and pressure, video, and other environment data if and when available such as other medical devices connected 3 that provide essential information about the start and stop of the data valid session 6. Medical devices 1 usually have one or more data export mechanism 7 which is used from a Medical Device Data Systems (MDDS) 8a to extract and collect ALL possible data, along with metadata 2, 3 from specific software and hardware drivers and interfaces 9 and along with previously associated 10 location, metadata and clocktime 11 reference.

The MDDS stores 16 location sessions 15 with all medical data collected, metadata, timestamps and location identifiers 13 and keeps it for a limited time, for example up to 24 hours, before it copies it 20 to a centralized repository 18. Empty, non-relevant data 14 are simply not propagated and ignored.

The MDDS 8b can serve a complete time synchronized and location subset of near real time data 17 without intermediary subsystem, or if the complete dataset had been copied to a centralized repository 18, the past data subset 19 can be retrieved from the repository services 18.

Figure 4:
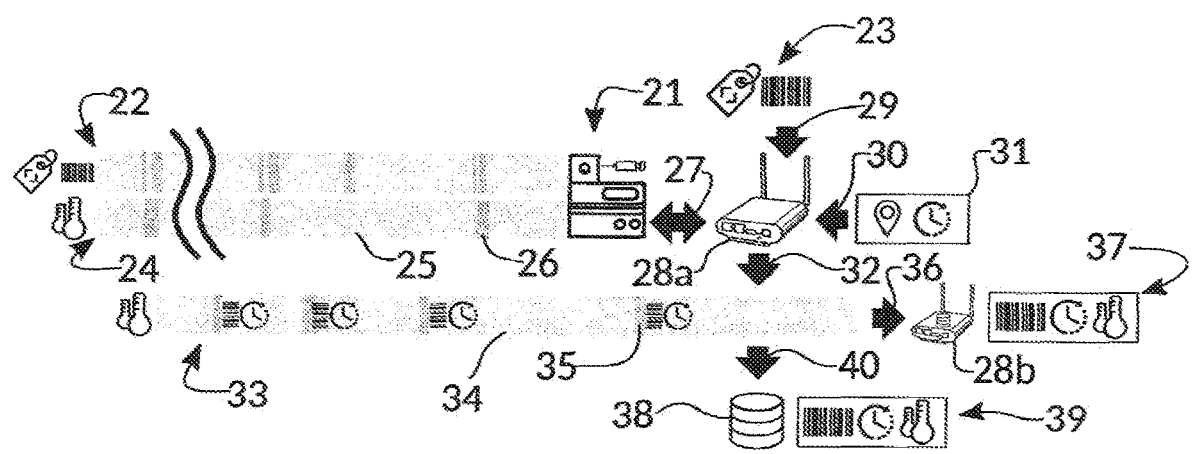
FIG. 4 is an illustration of the details of the recording of sporadic patient related data, part of the first layer of a MDGS, Digital Black Box Recording, in an embodiment.

FIG. 4 is a block diagram illustrating details of another component of Layer (1) Digital Black Box Recording, in particular, medical devices that measure sporadic patient related data 21 such as blood gas laboratory machines, generic laboratory devices, portable non invasive blood pressure devices, scales and similar belonging to the "spot" group of potentially retrievable medical data 24. The session beginning, duration and result can be directly associated from meta-data, such as bar code patient ID, Point Of Care (POC) input, and the result 26. Previous idle, non-patient data that is irrelevant and does not provide any information is not propagated, except for the metadata indicating that at that time patient data results were not being collected 25. Metadata is included such as, but not limited to, Patient Bar Code ID, POC input, device not ready, cable disconnected, device powered off 2, but also room temperature and pressure, video, and other environment data such as other medical devices connected 3 that provide essential information about the start and end of the result data 26. Medical devices and Laboratory devices 21 usually have one or more data export mechanism 27 which is used from a Medical Device Data Systems (MDDS) 28a to extract and collect ALL possible data, along with Metadata 22, 23 from specific software and hardware drivers and interfaces 29 and along with previously associated 30 location, metadata and clock-time reference 31.

The MDDS stores 36 location sessions 35 with all medical data collected, metadata, timestamps and location identifiers 33 and keeps it for a limited time, for example up to 24 hours, before it copies it 40 to a centralized repository 38. Empty, non-relevant data 34 are simply not propagated and are ignored.

The MDDS can serve a complete time synchronized and location subset of near real time data 37 without intermediary subsystem, or if the complete dataset had been copied to a centralized repository 38, the past data 39 subset can be retrieved from that repository service 38.

In any case, the Layer (1) Digital Black Box Recording does not have Protected Health Information (PHI), and if it is provided, it is stripped off and eliminated from the stored data. The possible PHI is removed from drivers handling specific medical devices.

Block Chain Signature Anti Tampering Protection

Figure 5:
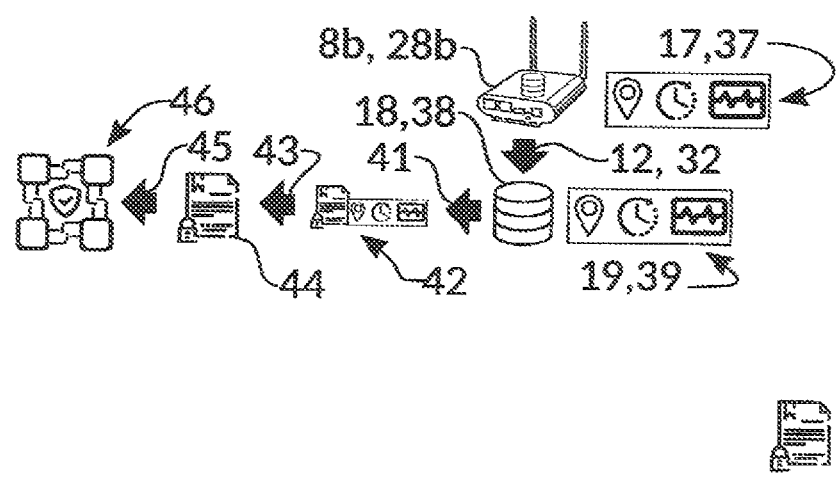
FIG. 5 is an illustration of the details of providing block chain signatures for black box recorded patient data sets in an embodiment.

When the MDDS 8b, 28b transfers the complete time synchronized and location data set 17, 37 to a centralized repository 18, 38, then as depicted in FIG. 5, the past data set 19, 39 is "signed" 41, 42, and the signature 44 is produced 43. The signature can be transferred 45 or stored to the external Block Chain Server Authority 46 to tamper proof the data collected and have an external safety check for data consistency.

Electronic Black Box Recording Data Diagrams for Various Medical Data and Medical Relevant Data Sources.

Figure 6:
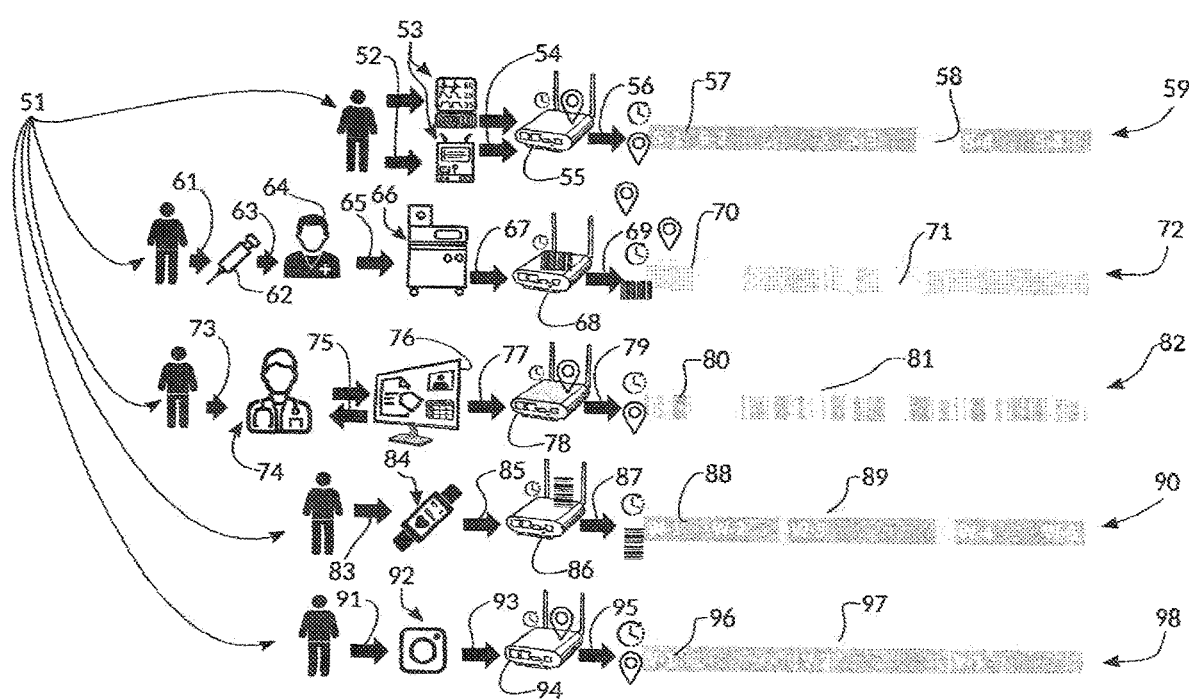
FIG. 6 is an illustration of the details of black box recording of a variety of different types of patient data in an embodiment.

Different medical and medical relevant data types are recorded, including location and patient ID metadata, and time synchronized with medical device data as depicted in FIG. 6. Continuous medical devices 59, laboratory devices 72, professional journaling and comments 82, personal wearables and fitness trackers 90, and video capture systems 98 store the non PHI (Protected Healthcare Information) only.

Continuous Medical Measurements

When patients 51 are connected with physical sensors and leads 52 to medical devices 53 that have the capability to export real or near real time data 54 to an MDDS 55, the MDDS 55 will timestamp, location and metadata associate the data created 56 with a Digital Black Box Recorder dataset 59 consisting of different data sessions 57 and idle time 58.

Laboratory Data

Samples of blood or other patient relevant organic samples 61 are taken and temporary conserved 62 and transported 63 by healthcare professionals 64 then properly processed and electronically identified 65 by laboratory device 66. The lab equipment should have the ability to export metadata such as POC or ID-collected and lab results in an electronic format 67 which is collected and processed by the MDDS 68. The MDDS will timestamp, location, ID and metadata associate the data creating 69 a Digital Black Box Recorder dataset 72 consisting of different laboratory results 70, metadata of patient identification codes and idle time 71. Protected Healthcare Information is stripped off to assure the data is deidentified, matching a single universal identification code to be stored instead if not already provided.

Medical Journaling

Every patient 51 consult, visit or opinion 73 between patient 51 and the medical professional 74 can be recorded or have notes taken 75 by third party software or systems 76 and directly exported or queried 77 from the MDDS 78 systems at the place of creation (near the patient current location). The MDDS will timestamp, location, ID and metadata associate the data, creating 79 a Digital Black Box Recorder dataset 82 consisting of various notes and documents, video and audio notes 80, metadata of patient identification codes and idle time 81. Protected Healthcare Information will be stripped off and assure the data is deidentified matching a single universal identification code to be stored instead.

Wearables and Fitness Trackers

Patient 51 might have 83 various personal wearable devices operating with BLE (blue tooth low energy or similar technologies) 84 that can be periodically or constantly in communication 85 with a fixed or portable MDDS or personal phone MDDS app 86 that has been preprogramed with a BLE MAC address to receive and associate the medical devices with the patient. Like the continuous medical measuring 59 and the measure-result laboratory systems 72, data sessions are defined 87 with metadata such as MAC, location and the receiving MDDS ID 88 and not-relevant data segments 89.

Video and Medical Relevant Data

All patient 51 relevant video or medically relevant ambient data 92 can be recorded 93, time and location synchronized by the MDDS 94 system. The MDDS will timestamp, location and metadata associate the video and/or ambient data creating 95 a Digital Black Box Recorder video or ambient dataset 98 consisting of different data session 96 and idle time 97.

Figure 7:
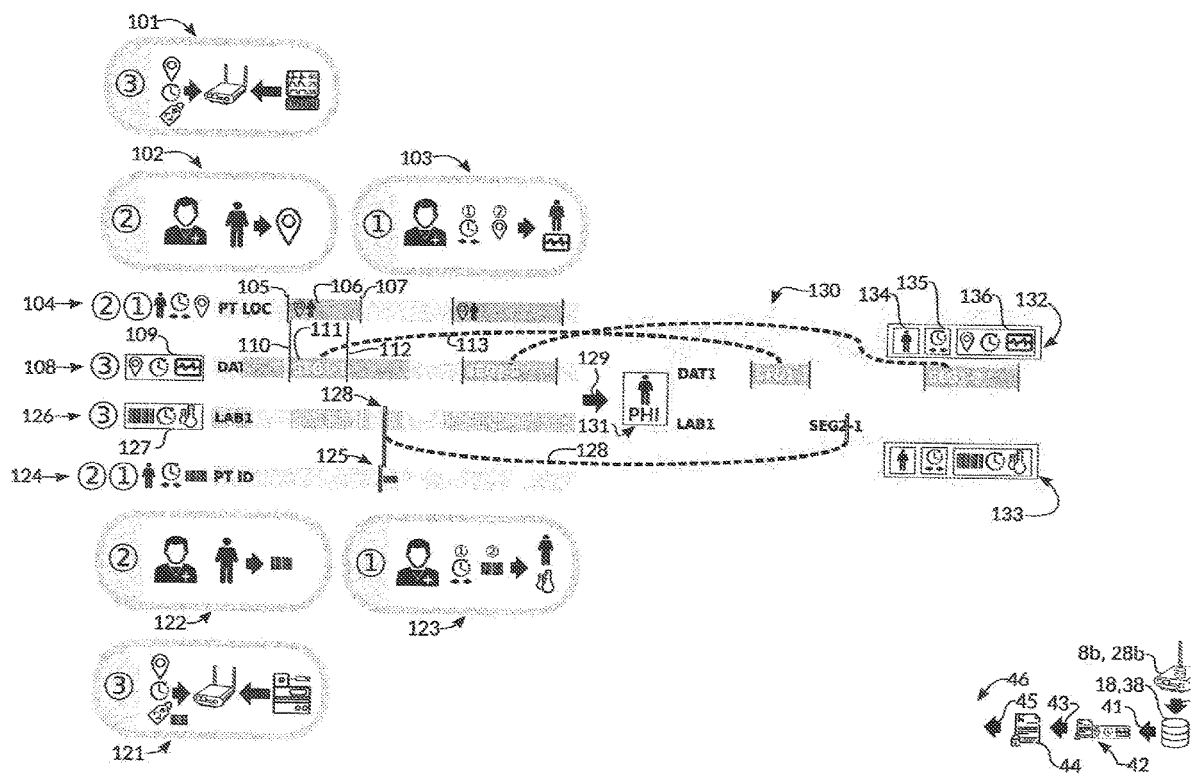
FIG. 7 is an illustration of the details of the second layer of a MDGS, Positive Patient Identification and Data Verification in an embodiment.

Second Layer of Medical Data Governance: Positive Patient Identification and Data Validation FIG. 7 shows the process of association between the patient and the data collected, or to be collected 101, 121. An external process, software or system, associates a Patient Identification code to a location 102 or patient-to-patient Identification code 122. An active healthcare professional, or someone that has been assigned to verify the patient data, patient location or patient identification, confirms the three key elements of the patient data triplets: patient identification and its code 134, segment or segments of time the patient was on location 135, and patient data collected at that location 109, 136 throughout the active process 103, 123.

Due to patient location recorded or provided by third party systems 102, 104 and data and metadata collected 101, 108, a subsection defined by start 105 and stop time 107, identified by a healthcare professional 106 or by third-party systems allows the precise selection of the appropriate and consistent data session 111 and seamlessly finetunes the accurate start 110 and stop 112 of the particular data session 113, then creates the building block of triplets 132 that constitutes a complete positive patient identification and data validation record 130.

For a laboratory, or multi patient systems such as laboratory machines, an action that immediately precedes or clearly relates to the result being consecutively transferred and collected by the MDDS system 121, a previously created Patient Identification code 122 is collected as metadata and time synchronized with the result that is collected. An active process of confirming the data 128, patient and patient id 125, and validity of test result 123 creates the triplets 133 from the data set recorded 126 and the patient, time segment and location information 124.

Protected Healthcare Information and Anti Tampering with Block Chain Signature

Figure 8:
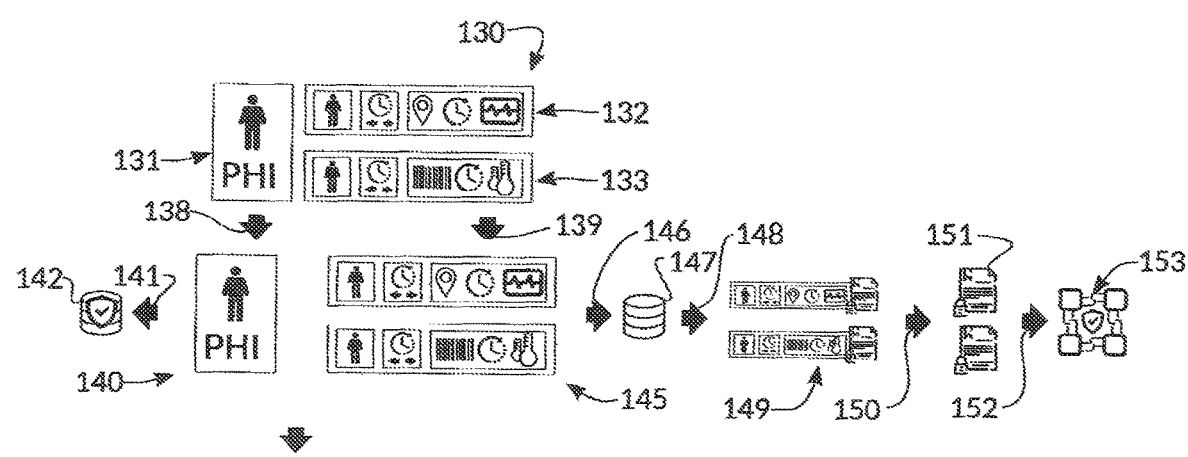
FIG. 8 is an illustration of the details of the process of storing Protected Healthcare Information (PHI) and providing a PHI data set with a block chain signature.

As depicted in FIG. 8, the process of active Positive Patient Identification and Data Validation creates multiple patient time segment data records 132, 133 associated with the patient 130 where PHI is shown, visible 131 and essential for positive patient association and the data validation process. After the modification of the previous data segments due to different information such as different times or location association, or upon creation of new triplets, they are stored 139 separately 145 from the storing 138 of the PHI 131. PHI 131 is stored 138 on third party systems 140, 141 running on a protected database system 142.

Upon confirmation of the triplet's association 145, each triplet is recorded 146 on a database 147 that triggers an automatic digital signature of each record 149 and a signature certificate is transferred 150, 151 and delivered 152 to the third party Block Chain system 153 for safety and anti-tamper proofing of the data.

Medical Data Outputs and Deidentified Research Data Exports

Figure 9:
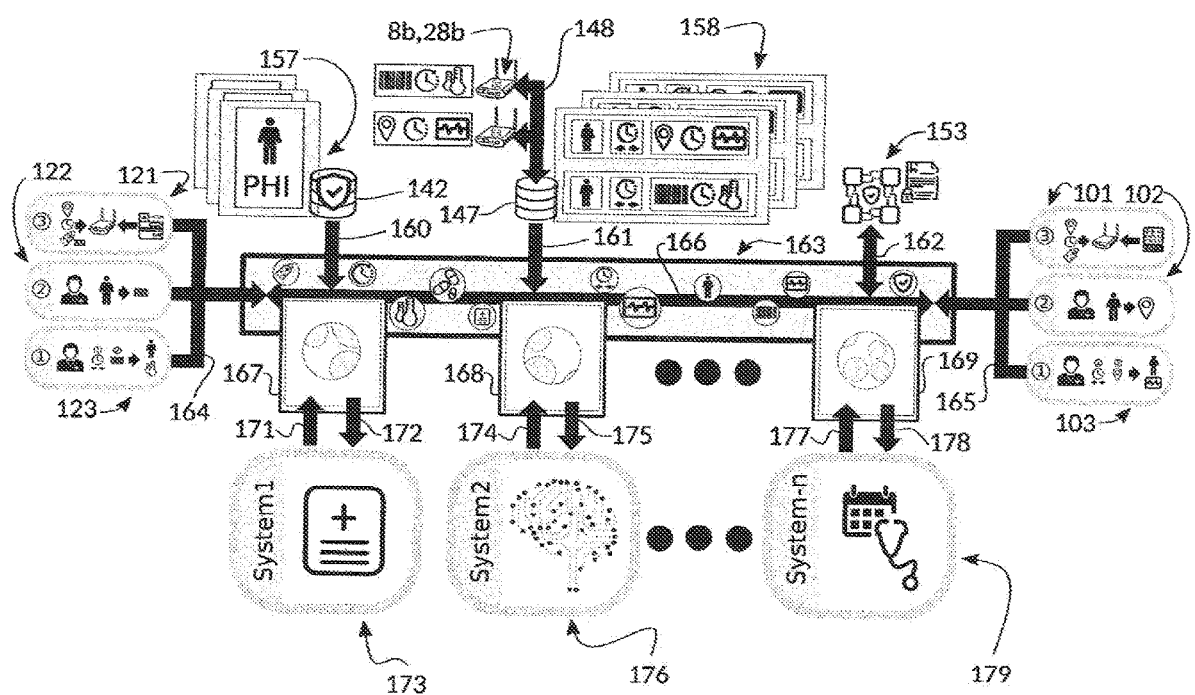
FIG. 9 is an illustration of the details of the third layer of a MDGS, data extraction and export, in an embodiment.

The third layer of the Medical Data Governance System is data extraction and single point of truth for legacy and future healthcare data systems. As depicted in FIG. 9, dependencies for adequate data outputs are defined as follows: the database 147 is populated with multiple 158 patient associated data session records 145, and the different PHI data 157 are also recorded and protected from non-authorized use 142 and interfaced to the MDGS 160. A Block Chain external service 153 is used to prevent data tampering and interfaced to the MDGS 162. Real time data is available through secure proxy tunnel 148 from bedside MDDS systems 8b, 28b. Previous location and proper time reference, metadata drivers and medical device drivers are set and ready 101. Drivers for barcode or POC inputs are properly installed to the MDDS system 8b, 28b, connected to laboratory, spot-like, multi patient medical systems 121. Patient ID is coded to barcode or POC patient code from third party systems and is available for research 122. Patient locations are available from third party systems or documented 102. Active healthcare professional(s) or an adequate automated system is assigned to verify and confirm patient id, location or barcode ID, time span, and to validate the collected data 123, 103.

True Source of Data and Data Export

As depicted in FIG. 9, by concentrating all available medical relevant data into a single source designed to handle very large, different data formats (data, metadata, values, trending, waveforms, video etc.) and providing a subset of data to each receiving subsystem 173, 176, 179 with the correct source and time reference, the Medical Data Governance System becomes the True Source of Data and guarantees the data consistency through the use of block chain signatures.

Due to the exponential data availability from growing health related devices, the risk of data not being collected, or worst being wrongly associated grows exponentially. The Medical Data Governance System opposes this trend by using the same data to augment the data affinity and isolate and indicate a possible association or data integrity errors.

An MDGS 163 data export subsystem with specific, recorded, and real time data in relation to location or to patient source can be configured 167, 168, 169 for output system 173, 176, 179. Internal to a MDGS export data sub-item, a backbone of all data is available 166 for export drivers 167, 168, 169 access. For example, a minute-based representative value subset for a patient can be configured (exported to EMR, along with the triplets Unique Identifiers (IUD) for later more in-depth review 173, 176, 179 through a different export driver. Selected high frequency, high accuracy data can be exported, after a prolonged period like 30 or 60 days, to AI systems for machine learning processes 173, 176, 179.

In essence, data export of the same complete data acquired from medical devices 167, 168, 169 can be different depending on the different requirements of exporting systems, and the export drivers and protocols 171, 172, 174, 175, 177, 178 can be created on demand from original, complete, high frequency, high fidelity, rich data sets stored in Digital Black Box records, time synchronized and with positive patient identification and data validation.

Although particular embodiments have been described in this disclosure, many other variations and modifications will be apparent to those skilled in the art. Thus, the instant invention can be defined and limited only by the claims to be associated with this application.

The invention claimed is:

1. A method for collecting, storing, and making available complete and accurate medical patient data, comprising the steps of:

recording various types of patient data using digital black boxes;

identifying individual patients from the various types of patient data and validating the various types of patient data obtained from the digital black boxes to create sets of identified and validated data;

storing said sets of identified and validated data in a central repository;

analyzing the sets of identified and validated data and removing personalized healthcare information therefrom to create the complete and accurate medical patient data; said analyzing step including the step of analyzing data affinity and isolating and identifying association and data integrity issues; and, normalizing the complete and accurate medical patient data by generating a specific export driver for each of said receiving medical subsystems, each of said specific export drivers collecting, filtering, and consistency checking the complete and accurate medical patient data to at least two receiving medical subsystems;

wherein said at least two receiving medical subsystems have different data receipt formats, each of said export drivers formatting said data for receipt by one of said receiving medical subsystems.

2. The method of claim 1 wherein at least one of said various types of patient data is high frequency data.

3. The method of claim 1 wherein one of said receiving medical subsystems is an AI system utilizing machine learning processes.

4. The method of claim 2 wherein said high frequency data is extracted from said various types of data for use in an AI system utilizing machine learning processes.

5. A method according to claim 1, wherein a medical device data system is used to record the patient data.

6. A method according to claim 5, wherein the medical device data system provides the various types of patient data to a positive patient identification and data validation system.

7. A method according to claim 6, wherein the various types of data include environmental conditions present when the data was acquired.

8. A method according claim 1 wherein said various types of patient data are time stamped.

9. A method according to claim 1 wherein said various types of patient data are associated with a location.

10. The method of claim 1 wherein each of said sets of data include patient identification and a patient identification code, a segment or segments of time the patient was at a particular location, and patient data collected at the particular location and further including the step of having human verification of each of said sets.

11. The method of claim 1 wherein the step of analyzing data affinity includes the step of human verification of each of said sets of data to find association and time segment errors.

12. The method of claim 11 wherein each set of data having association or time segment errors is corrected and signed with blockchain to produce a corrected set of data, and the corrected set of data is sent to one of said receiving medical subsystems.

* * * * *